(12) United States Patent
Kuvshinov et al.

(10) Patent No.: US 7,910,803 B2
(45) Date of Patent: Mar. 22, 2011

(54) **TRANSFORMATION IN *CAMELINA SATIVA***

(75) Inventors: Viktor Kuvshinov, Vantaa (FI); Anne Kanerva, Itasalmi (FI); Kimmo Koivu, Itasalmi (FI); Svetlana Kuvshinova, Vantaa (FI); Eija Pehu, Helsinki (FI)

(73) Assignee: Unicrop Oy, Helsinki (FI)

( * ) Notice: Subject to any disclaimer, the term of this patent is extended or adjusted under 35 U.S.C. 154(b) by 0 days.

(21) Appl. No.: 12/288,791

(22) Filed: Oct. 23, 2008

(65) Prior Publication Data

US 2009/0151028 A1 Jun. 11, 2009

Related U.S. Application Data

(62) Division of application No. 10/416,091, filed as application No. PCT/FI01/00978 on Nov. 12, 2001, now abandoned.

(30) Foreign Application Priority Data

Nov. 13, 2000 (FI) .......................................... 110009

(51) Int. Cl.
*A01H 1/00* (2006.01)
*C12N 15/82* (2006.01)
(52) U.S. Cl. ....................................... 800/294; 435/469
(58) Field of Classification Search .................. 800/294; 435/469

See application file for complete search history.

(56) References Cited

U.S. PATENT DOCUMENTS 5,463,174 A * 10/1995 Moloney et al. .............. 800/294
5,750,871 A 5/1998 Moloney et al.

OTHER PUBLICATIONS de Block et al. Transformation of Brassica napus and Brassica oleracea using Agrobacterium tumefaciens and the expression of the bar and neo genes in the transgenic plants. Plants Physiol. (1989) 91, 694-701.*
Puchta. Removing selectable marker genes: taking the short cut. 2000 Elsevier Science Ltd. vol. 5, No. 7, 273-274.*
Tattersall et al. Establishment and in vitro regeneration studies of the potential oil crop species Camelina sativa. Plant Cell, Tissue and Organ Culture 55: 147-149, 1999.*
Petri et al. An antibiotic-based selection strategy to regenerate transformed plants form apricot leaves with high efficiency. Plant Science 175 (2008) 777-783.*
Tattersall A. and Millam S. 1999 Establishment and in vitro regeneration studies of the potential oil crop species Camelina sativa. Plant Cell, Tissue & Organ Culture 55:147-149.

* cited by examiner

*Primary Examiner* — June Hwu
(74) *Attorney, Agent, or Firm* — Dodds and Associates; Leea S. Somersalo; John Dodds

(57) ABSTRACT

The present invention relates to plant biotechnology and specifically to a method for genetically transforming *Camelina sativa* with *Agrobacterium*-mediated transformation system. It comprises *Camelina sativa* for producing homologous and heterologous recombinant products including oil and protein products and assessing and screening the efficacy of plant transformation. Also disclosed are transgenic *Camelina sativa* plants, seeds as well as cells, cell-lines and tissue of *Camelina sativa*.

10 Claims, 6 Drawing Sheets
(3 of 6 Drawing Sheet(s) Filed in Color)

TRANSFORMATION IN *CAMELINA SATIVA*

This is a divisional application of U.S. patent application Ser. No. 10/416,091 filed Sep. 8, 2003 now abandoned, which is a national stage application of international application PCT/FI01/00978 filed Nov. 12, 2001 which claims priority of national Finnish patent number FI110009. filed on Nov. 13, 2000.

TECHNICAL FIELD OF THE INVENTION

The present invention relates to plant biotechnology and plant cell transformation. More particularly the invention relates to a method for genetically transforming *Camelina sativa* using *Agrobacterium*-mediated transformation of a plant tissue explant and subsequent regeneration of the transformed cells into whole *Camelina sativa* plants. It further relates to the use of an *Agrobacterium*-mediated transformation method of *Camelina sativa* for producing homologous or heterologous recombinant products including proteins, enzymes and oil products and for assessing and screening the properties, and effects of DNA sequences and recombinant DNA constructs in plants.

BACKGROUND OF THE INVENTION

Genetic transformation of plants allows the introduction of genes of any origin into the target species providing novel products for e.g. agricultural, horticultural, nutritional and chemical applications. Furthermore, transgenic plants provide more information about basic plant biology, gene function and regulation. In many plant species, traditional plant breeding is limited due to the fact that the existing gene pool is narrow and prevents further development. Alteration of single characteristics can be time-consuming and even impossible without changing any other properties. Major applications of genetic transformation focus on the improvement of for example disease resistance, insect resistance, herbicide tolerance, modified quality characteristics such as modification of oil and protein compositions as well as on improving stress tolerance and modifying growth characteristics. In other applications transgenic plants are used as bioreactors for producing foreign proteins or plant secondary metabolites.

Several vector systems have been developed to be used in higher plants for transferring genes into plant tissue e.g. the use of plant viruses as vectors, direct gene transfer using DNA fragments not attached to a vector and *Agrobacterium*-mediated gene transformation.

*Agrobacterium*-mediated gene transformation is the most widely used method to transfer genes in plants using either *Agrobacterium tumefaciens* or *Agrobacterium rhizogenes*. Several *Agrobacterium*-mediated systems and methods for transforming plants and plant cells have been disclosed for example in WO 84/02920, EP 289478, U.S. Pat. No. 5,352,605, U.S. Pat. No. 5,378,619, U.S. Pat. No. 5,416,011, U.S. Pat. No. 5,569,834, U.S. Pat. No. 5,959,179, U.S. Pat. No. 6,018,100, and WO 00/42207.

Many of said methods are especially applied for oil crops such as Brassicaceae including *Brassica rapa* ssp. *oleifera* (Radke et al., Plant Cell Rep. 11:499-505, 1992) and *Brassica campestris* (Kuvshinov et al. Plant Cell Rep. 18:773-777, 1999). U.S. Pat. No. 5,188,958, U.S. Pat. No. 5,463,174 and U.S. Pat. No. 5,750,871 disclose the transformation of *Brassica* species using *Agrobacterium*-mediated transformation system. However, the conditions described in these publications do not give successful transformation result with *Camelina sativa*.

Several transformation strategies utilizing the *Agrobacterium*-mediated transformation system have been developed. The binary vector strategy is based on a two-plasmid system where T-DNA is in a different plasmid from the rest of the Ti plasmid. In the cointegration strategy a small portion of the T-DNA is placed in the same vector as the foreign gene, which vector subsequently recombines with the Ti plasmid.

The production of transgenic plants has become routine for many plant species, but no universal transformation method for different plant species exists, since transformation and regeneration capacity varies among species and even with different explants. However, there is a need for developing alternative transformation systems and methods especially in oil crop. *Camelina sativa* (gold of pleasure or false flax), one of the most important oil crops in Europe during bronze and iron age, has been grown in Europe for centuries. It was especially used to production of lamp oil, but also in edible products. Oil products obtained from *Camelina sativa* have been used for producing food spreads as described in the U.S. Pat. No. 6,117,476.

*Camelina sativa* (L. Crantz) belongs to the family Brassicaceae in the tribe Sisymbrieae and both spring- and winter forms are in production. It is a low-input crop adapted to low fertility soils. Results from long-term experiments in Central Europe have shown that the seed yields of Camelina sativa are comparable to the yields of oil seed rape.

Due to the high oil content of *Camelina sativa* seeds varying about 30-40%, there has been a renewed interest in *Camelina sativa* oil. *Camelina sativa* seeds have a high content of polyunsaturated fatty acids, about 50-60% with an excellent balance of useful fatty acids including 30-40% of alpha-linolenic acid, which is omega-3 oil. Omega-3 oils resemble marine oils and are rarely found in other oil crops. Furthermore, *Camelina sativa* seed contains a high amount of tocopherols (appr. 600 ppm) with a unique oxidative stability. Moreover, the oil is low in glucosinolates (Matthäus and Zubr, Industrial Crops and Products 12:9-18, 2000). A quality problem for food and feed uses of *Camelina sativa* is that it contains relatively high amount of erucic acid (2-4%) and 11-eicosenoic acid (gondoic acid). Erucic acid is poorly digested and causes myocardial lesions in animals. Said problem causing erucic and 11-eicosenoic acids can be removed from the oil and used for other non-nutritional applications, which include the use of high-erucic acid containing oils as lubricants. Industrial applications might require prominence of such fatty acid of singular importance.

As *Camelina sativa* is a minor crop species, very little has been done in terms of its breeding aside from testing different accessions for agronomic traits and oil profiles. A mutation breeding experiment to induce variation in the fatty acid profiles has reported three to four fold differences (Buchsenschutz-Northdurft et al., 3rd European Symposium on Industrial Crops and Products, France, 1996). Applications of tissue culture techniques to *Camelina sativa* are restricted to two approaches. *Camelina sativa* has been used in a somatic fusion with other *Brassica* species (Narasimhulu et al., Plant Cell Rep. 13:657-660, 1994; Hansen, Crucifer. News 19:55-56, 1997; Sigareva and Earle, Theor. Appl. Genet. 98:164-170, 1999) and regenerated interspecific hybrid plants were obtained (Sigareva and Earle, Theor. Appl. Genet. 98:164-170, 1999). Recently, *Camelina sativa* shoots have been regenerated from leaf explants (Tattersall and Millam, Plant Cell Tissue and Organ Culture 55:147-149, 1999).

Present invention provides a genetic transformation system for *Camelina sativa*, which would address rapid improvement of this crop for different end-uses, which include the production of homologous and heterologous recombinant DNA products. Examples of homologous recombinant products comprise e.g. unique protein or oil products which are specific for *Camelina sativa*, whereas heterologous products include foreign proteins, enzymes, etc.

Another embodiment of the present invention is to provide a novel model plant for replacing e.g. *Arabidopsis* and tobacco.

A further embodiment is to provide transgenic *Camelina sativa* plants, plant tissue, plant cells and cell lines and seed.

SUMMARY OF THE INVENTION

The objectives of the present invention are achieved by the method of the present invention, which enables the use of *Agrobacterium*-mediated transformation method for genetic transformation of *Camelina sativa* explants.

The specific advantage of the present method is that *Camelina sativa* has characteristics which make it suitable for use in efficient genetic transformation and subsequent production of heterologous and homologous gene products. *Camelina sativa* germinates and grows rapidly and already after 10 days from germination explants can be excised from plantlets. Genetically transformed *Camelina sativa* plants can be transferred to greenhouse after four weeks from transformation event. The transformation efficiency of *Camelina sativa* is high compared to other plants including *Brassica* species. The rapid growth of *Camelina sativa* enables that the transformation method can be scaled up for future applications.

Transformation of *Camelina sativa* is effective even without selection, avoiding the use of a selectable marker gene, which makes the transformation of *Camelina sativa* attractive for applications, since possible harmful effects of the marker genes used in cloning vectors is a concern in genetically engineered plants.

The present invention provides a novel method to genetically transform *Camelina sativa* using *Agrobacterium*-mediated transformation. The method and the products and means utilized in said method are as defined in the claims of the present invention and they provide an efficient, reliable and convenient transformation system for producing *Camelina sativa* crop with improved properties using transgenic improvement and recombinant DNA technologies.

The present invention is related to transgenic *Camelina sativa* plants obtainable with the method of the present invention as defined in the claims by optionally sterilizing one or more seeds of *Camelina sativa* and germinating and growing said seeds into plants, providing explants of Camelina sativa plants, contacting the explants of *Camelina sativa* with an *Agrobacterium* vector comprising at least one recombinant DNA construct, an optional selectable marker gene and an optional enhancer, allowing the transformation to take place on a cell culture medium optionally supplemented with at least one hormone and/or growth factor, selecting the transformed tissue of *Camelina sativa* on a medium optionally containing at least one selective component, inducing the regeneration of one or more shoots from the transformed explants on a cell culture medium optionally containing at least one hormone and/or growth factor and growing the shoots into whole *Camelina sativa* plants.

The invention is also related to transgenic *Camelina sativa* plant tissue obtainable with the method defined in the claims.

The invention further relates to transgenic *Camelina sativa* plant cells or cell lines obtainable with the method defined in the claims.

The invention is also related to transgenic *Camelina sativa* seed obtainable with the method defined in the claims.

A SHORT DESCRIPTION OF THE DRAWINGS

The patent or application file contains at least one drawing executed in color. Copies of this patent or patent application publication with color drawing(s) will be provided by the U.S. Patent and Trademark Office upon request and payment of the necessary fee.

Figure 4:
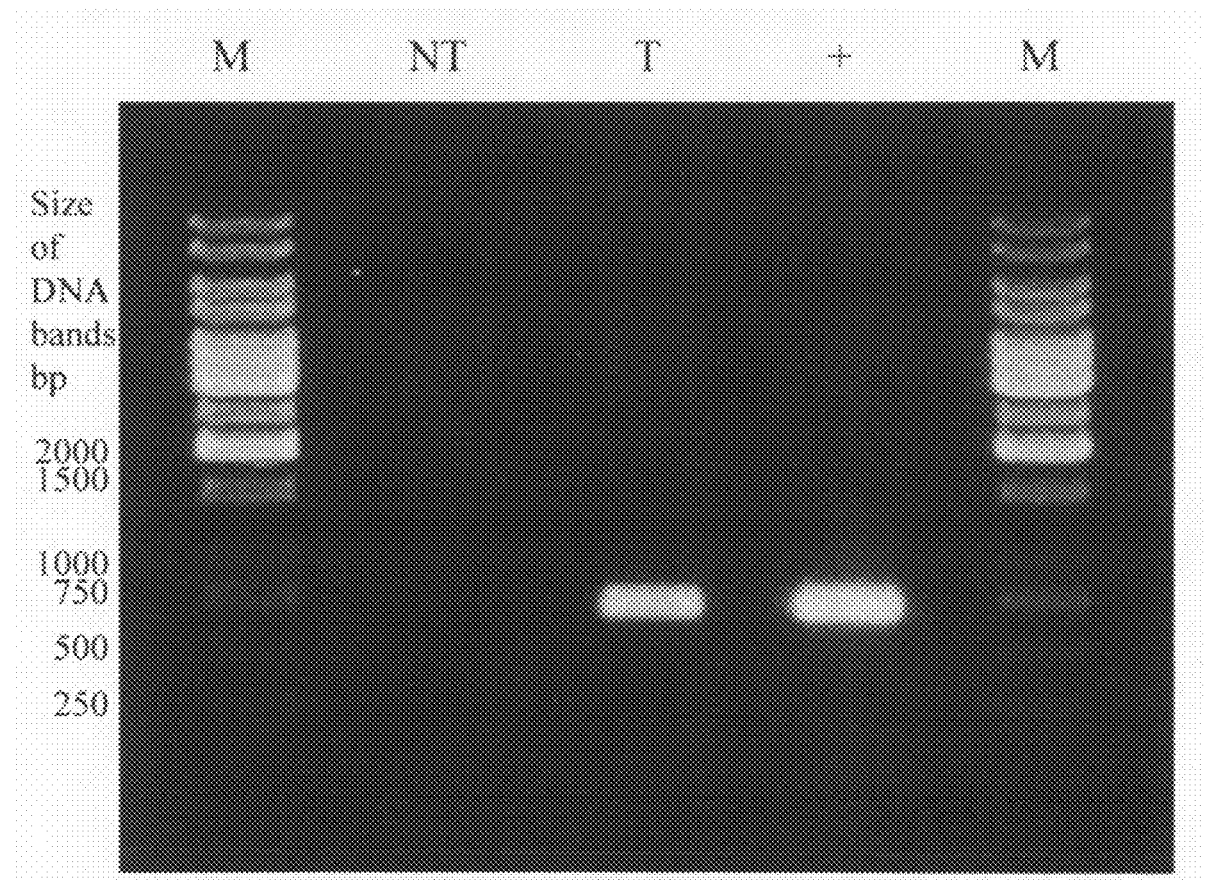

FIG. 4 shows results of PCR amplification of a transgenic insertion. The PCR was carried out using specific primers developed for the central part of uidA gene. The length of the DNA sequence between the primers is about 700 nucleotides and thus the size of the amplification product is also 700 nucleotides. Samples on the gel are marked as follows: NT, non-transgenic *Camelina sativa* (negative control); T, transgenic GUS positive line of *Camelina sativa* expressing uidA gene; +, uidA gene sequence cloned in pBluescript vector as positive control. M is a one kilobase (1 kb) marker ladder (Fermentas). The sizes of some of the marker bands are shown on the left side of the figure. No PCR product was obtained when non-transgenic *Camelina sativa* DNA was used as template, whereas when using transgenic *Camelina sativa* an amplification product of 700 nucleotides corresponding to the positive control was obtained.

Figure 5:
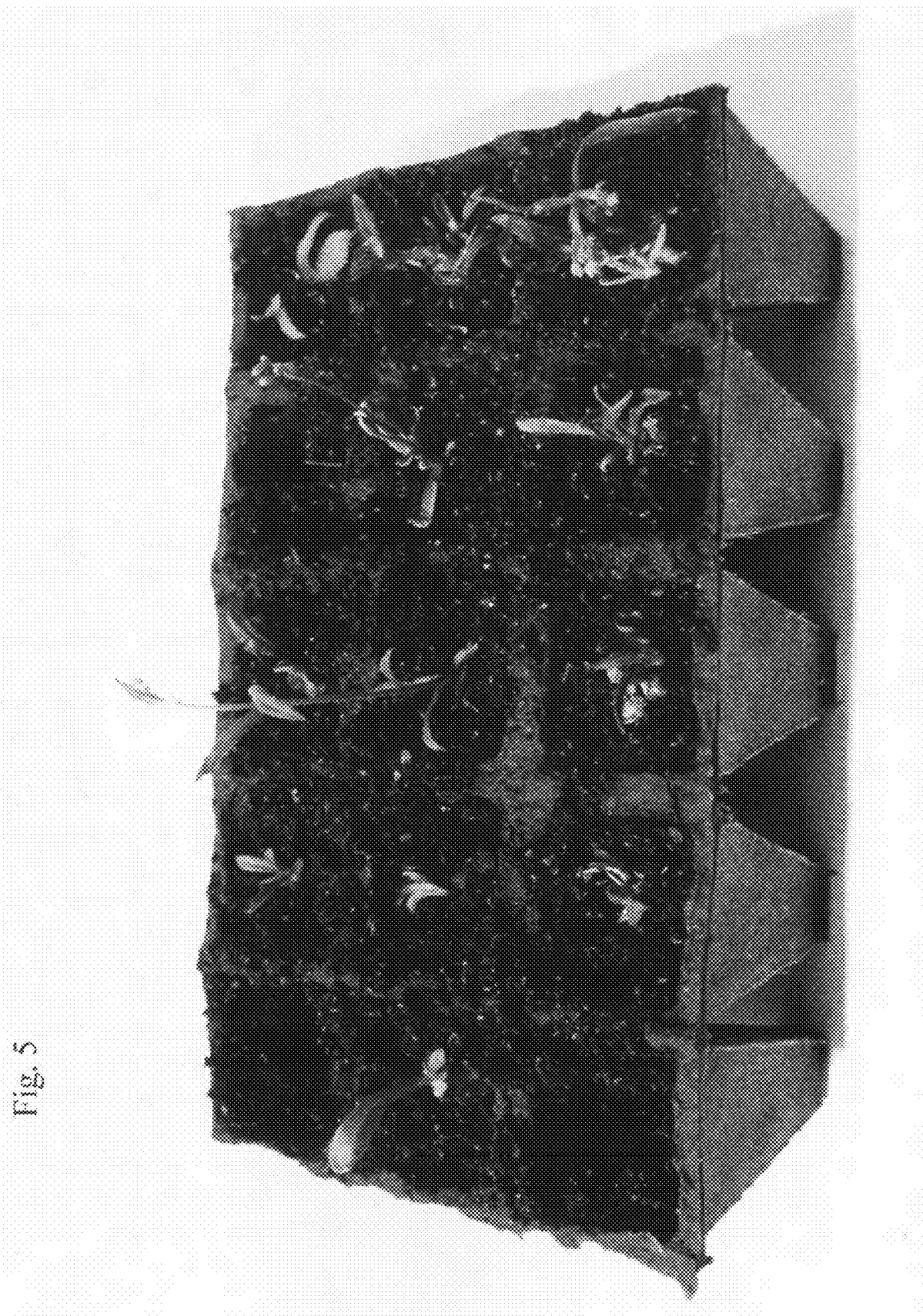

FIG. 5 shows *Camelina sativa* plantlets grown in greenhouse conditions. The plantlets are from transgenic shoots recovered and rooted after in vitro selection of transformed explants of *Camelina sativa*.

DETAILED DESCRIPTION OF THE INVENTION

In the present invention the terms used have the meaning they generally have in the fields of conventional plant breeding, plant biochemistry and production of transgenic plants, including recombinant DNA technology as well as agriculture and horticulture. Some terms, however, are used with a somewhat deviating or broader meaning in this context. Accordingly, in order to avoid uncertainty caused by terms with unclear meaning some of the terms used in this specification and in the claims are defined in more detail below.

ABBREVIATIONS

| | |
|---|---|
| BAP | 6-benzylaminopurine |
| 2,4-D | 2,4-dichlorophenoxyacetic acid |
| GUS | β-glucuronidase (uidA reporter gene) |
| Hpt | gene encoding for hygromycin phosphotransferase |
| Hyg | hygromycin |
| IAA | indole-3-acetic acid |
| Kan | kanamycin |
| MS | Murashige and Skoog medium |
| NAA | α-naphthaleneacetic acid |
| nptII | gene encoding for neomycin phosphotransferase II |

| | |
|---|---|
| Rif | rifampicin |
| Spe | spectinomycin |
| Str | streptomycin |
| Tc | ticarcillin |
| uidA | gene encoding for β-glucuronidase (GUS) |
| YEB | medium for cultivation of *Agrobacterium* cells |

DEFINITIONS

"*Camelina sativa*" belongs to the family of Brassicaceae in the tribe Sisymbrieae. The seed yields of *Camelina sativa* are comparable to the seed yields of oil seed rape. Useful varieties of Camelina sativa are for example var. Calina and var. Calinca.

The term "*Agrobacterium*" means *Agrobacterium tumefaciens, Agrobacterium rhizogenes* or another *Agrobacterium* species useful for genetic transformation of plants to produce genetically modified plants.

"*Agrobacterium tumefaciens*" is a naturally occurring bacterium which when containing a circular Ti (Tumor inducing) plasmid is able to form crown gall disease in many species of dicotyledonous plants. Crown gall occurs when a wound is invaded by *Agrobacterium*. *Agrobacterium tumefaciens* natively has the ability to transfer a portion of its DNA called T-DNA, into the genome of the plant cells. In *Agrobacterium*-mediated transformation T-DNA is replaced with a foreign set of genes, thus, making the bacterium capable of transferring the foreign genes into the genome of the plant cell. "*Agrobacterium tumefaciens*" can be one of the three different strains of *Agrobacterium* used in the transformation of *Camelina sativa* or an equivalent strain suitable for the transformation. The strain LB4404 carries the plasmid pAL4404, the strain C58C1 carries the plasmid pGV3850 and the strain EHA105 carries the plasmid pTiBo542.

The term "*Agrobacterium*-mediated genetic transformation" in the present invention means that *Agrobacterium* is used as a vector which is able to transfer foreign gene(s) to *Camelina sativa* cells. The T-DNA portion of the Ti plasmid is replaced with the foreign gene and, after the *Agrobacterium* infection, transferred into the plant chromosomal DNA.

The term "transgenic plant" means a plant, especially *Camelina sativa* plant, which is obtained using the method disclosed in the present invention. The optionally sterilized seeds of Camelina sativa are germinated and grown to plants, which provide explants for use in *Agrobacterium*-mediated transformation method. An *Agrobacterium* strain containing an *Agrobacterium* vector comprising at least one recombinant DNA construct and an optional selectable marker gene is allowed to transform *Camelina sativa* cells in a cell culture medium optionally supplemented with at least one hormone and/or growth factor. Selection on a medium optionally containing at least one selective component is followed by the regeneration of one or more shoots or roots from the transformed explants on a cell culture medium optionally containing at least one hormone and/or growth factor. The shoots are grown into whole transgenic *Camelina sativa* plants.

The term "explant" means a part or a piece which is taken from a plant, in this context from *Camelina sativa*. These pieces or tissue explants can be excised from hypocotyl, cotyledon, stem, leaf or other plant organs and can be used for in vitro culture and for transformation experiments.

The term "in vitro explant" means a *Camelina sativa* explant excised from hypocotyl, cotyledon, stem, leaf or other plant organs originating from plants grown in vitro preferably under sterile conditions on culture media. An "explant" or "in vitro explant" can be a leaf segment.

The term "leaf segment" means a piece of leaf from preferably in vitro grown *Camelina sativa*. The leaves of in vitro grown *Camelina sativa* can be rather small in size for example 2-4 cm long and 0.5-1 cm wide. Accordingly, narrow leaves are cut across the leaf while larger leaves are also cut in half along the central vein.

The term "recombinant DNA construct" means a DNA sequence including linear or circular vector, plasmid or insert created by ligating or joining together pieces of DNA that are not normally contiguous in nature. The construct, which is transferred into the plant cell, comprises a specific gene of interest, which is desired to be introduced into the germline of the plant, and an optional selectable marker gene that confers upon the plant cell a resistance to a chemical selective component (selection agent).

The term "selectable marker gene" means an optionally used gene in plant transformation such as the gene for neomycin phosphotransferase (npt II), which expresses an enzyme conferring resistance to the antibiotic kanamycin and the related antibiotics neomycin, paromomycin, gentamicin, and G418, or the gene for hygromycin phosphotransferase (hpt), which expresses an enzyme conferring resistance to hygromycin. Other selectable marker genes include genes encoding herbicide resistance, metal resistance or sensitivity, for example Cu-resistance or sensitivity, genes utilizing special carbohydrate sources or other metabolites including for example mannose or other selection systems.

The term "selection of the transformed tissue of *Camelina sativa*" means that the transformed tissue is grown on a medium containing a substrate allowing the selection of transformed tissues which carry a marker gene. Preferred selective substances are antibiotics, for example hygromycin or kanamycin, but other selection systems such as herbicides, metal resistance or sensitivity, including e.g. Cu-resistance or sensitivity and special carbohydrate sources or other metabolites are applicable. The use of a marker gene e.g. hpt or nptII is optional, since possible harmful effects of the marker genes used with plant cloning vectors is one area of concern with genetically engineered plants. Antibiotic selection begins preferably immediately after transformation and the result of the selection can be seen in 1-2 weeks, when the explants begin to form callus.

The term "Murashige and Skoog (MS) medium or equivalent" or "MS medium or equivalent" means that preferably Murashige and Skoog's growth medium, that is MS medium, is used in the method of the present invention (Murashige and Skoog, Physiol Plant. 15:472-493, 1962). Any other medium suitable for the purposes of the present invention can also be used including for example the B5 medium. The growth medium can be in liquid form or made solid or semisolid using an appropriate amount of agar or gelrite for example 0.7 g/l. The concentration of the medium optionally varies from half strength to 2× strength.

The term "inoculation with *Agrobacterium*" means that the *Camelina sativa* explants are inoculated with bacteria by placing them in *Agrobacterium* suspension to enable the transformation of *Camelina sativa* with *Agrobacterium*. Before inoculation an overnight culture of *Agrobacterium* has been diluted in a Murashige and Skoog (MS) solution or another suitable growth medium to enable the transformation of *Camelina sativa* with *Agrobacterium*.

The term "co-cultivation" means that *Camelina sativa* explants are placed preferably on solid Murashige and Skoog (MS) agar medium or an equivalent medium supplemented with at least one hormone, such as cytokinin or auxin, and optionally with acetosyringone for co-cultivation. Explants are co-cultivated with *Agrobacterium* for time sufficient to enable the transformation, for example 2 days. During this step, the *Agrobacterium* transfers the foreign gene construct into *Camelina sativa* cells. The co-cultivated segments are then washed and placed on Murashige and Skoog (MS) medium or an equivalent for callus and shoot regeneration.

The term "shoot and root regeneration" means the induction of the formation of shoots and roots from the transformed explants where shoots appear on the explants after growing the explants on culture medium allowing shoot regeneration, preferably Murashige and Skoog (MS) medium or an equivalent, supplemented with hormones and/or growth factors allowing shoot and root regeneration, preferably cytokinin such as 6-benzylaminopurine (BAP) and auxin such as α-naphthaleneacetic acid (NAA) and an effective amount of substance capable of preventing the growth of contaminants, such as antibiotics carbenicillin or more preferably ticarcillin/clavulanic acid for time sufficient for shoots to appear.

The term "growing the shoots into a whole *Camelina sativa* plant" means that the regenerated transgenic shoots are grown and rooted for about 2-3 weeks on half strength Murashige and Skoog (MS) medium or an equivalent medium without hormones or optionally supplemented with auxins.

The term "hormones" and especially "plant hormones" or "growth factors" mean organic compounds or molecules originating in certain parts or organs of a plant, which compounds when transported to another tissue elicit a certain response. Plant hormones are active preferably in small concentrations and can be used in different combinations. The major classes of plant hormones are auxin, gibberellins, cytokinins, ethylene, and abscisic acid, each of which has many effects. Also a variety of other compounds including oligosaccharins, batasins and brassinosteroids function as hormones in plants. "Hormones", "plant hormones" and "growth factors" can be used as substances or means in the transformation method to enhance the transformation, selection, regeneration, growth or other functions.

Auxins can stimulate cellular elongation, differentiation of vascular tissue, fruit development, and formation of adventitious roots and production of ethylene. Naturally occurring and synthetic auxins include for example indole-3-acetic acid (IAA), 4-chloro-IAA, phenylacetic acid, α-naphthaleneacetic acid (NAA), 2,4-dichlorophenoxyacetic acid (2,4-D), indole-3-butyric acid (IBA), dimethylallylaminopurine (2iP) and other auxins.

Gibberellins (GA for gibberellic acid) can stimulate extensive growth of intact plants, the transition from juvenile to adult growth, bolting of biennials, fruit formation, and germination of some cereal grains. More than 80 gibberellins have been isolated from various fungi and plants including $GA_3$.

Cytokinins can stimulate cellular division, expansion of cotyledons, and growth of lateral buds. Cytokinins also delay senescence of detached leaves and, in combination with IAA, may influence formation of roots and shoots. Cytokinins include naturally occurring and artificial substances such as kinetin, zeatin, zeatin riboside, dihydrozeatin, isopentenyl adenine and 6-benzylaminopurine (BAP).

Ethylene is a gaseous hormone that can influence fruit ripening, abscission, sex expression, and the radial expansion of cells. Ethylene can also function as a "wound hormone". High amounts of ethylene are harmful, whereas low amounts promote rooting. Increased aeration of in vitro cultures removes ethylene.

Abscisic acid (ABA) is an inhibitor that can cause stomata to close, affects dormancy of some seeds, and, in general, counteracts the stimulatory effects of other hormones. These effects may occur because ABA is calcium antagonist.

The term "a system for carrying out *Agrobacterium* mediated genetic transformation in *Camelina sativa*" means a system which in a packaged combination is intended for commercial use. Said system comprises *Camelina sativa* seeds, suitable DNA sequences and/or DNA constructs, suitable media with optional additives and instructions for using the transformation system. The *Camelina sativa* seeds can be cultivated to provide the seedlings from which explants are taken. The DNA sequence is a homologous or heterologous additional foreign gene or part of a gene, as such, which encodes a desired product. The DNA sequences can also be provided as a DNA construct, in which case the foreign gene is functionally linked with one or more optional sequences, which are responsible for certain functions or capable of regulating said functions. Examples of such sequences are promoters or signal sequences. The DNA construct may comprise optional sequence allowing selection of explants of *Camelina sativa* carrying the transgenic inserts. The packaged combination can be provided with or without the media needed in the transformation procedure.

The term "assessing the efficacy of plant transformation" means the investigation of the rate of transgenic inclusions in transformed explants and is assessed by recording by visible means including GUS expression, PCR methods, Southern analysis or equivalent methods.

The term "homologous or heterologous recombinant products" means proteins, peptides, metabolites, oils, carbohydrates, polymers, or other products, which can be produced using *Agrobacterium* mediated transformation system in *Camelina sativa*. Homologous recombinant DNA products are produced when DNA sequences or genes native to *Camelina sativa* are used, whereas heterologous products are produced with DNA sequences or genes which are not naturally occurring in *Camelina sativa*. The "homologous and heterologous recombinant products" can originate from bacteria, viruses, fungi, plants and animals, including human proteins and peptides which require processing.

DETAILED DESCRIPTION OF THE INVENTION

*Brassica* species have been used as common model plants in plant breeding and molecular biology, but because they are prone to pests like *Meligethes aeneus*, an alternative plant related to them would be useful. *Camelina sativa* would provide such a new model plant, which is not sensitive to the pest. Furthermore, *Camelina sativa* has a relatively small genome, including only 20 chromosomes, which simplifies its use in genetic studies. Classically for example tobacco and *Arabidopsis* have been used as model plants and especially compared to *Arabidopsis*, Camelina sativa provides more plant material for further experiments.

We have examined different factors, which could have an effect on regeneration and transformation capacity of different explants of *Camelina sativa*. As a result we have developed a transformation method for plant explants, preferably leaf segments, of *Camelina sativa* plants grown in vitro using *Agrobacterium*-mediated transformation.

The present invention thus provides an *Agrobacterium*-mediated transformation method of Camelina sativa.

The starting material for the transformation is *Camelina sativa* seed. *Camelina sativa* plants producing seed are grown in greenhouse conditions, since field grown plants produce seed contaminated with bacteria, which later prevents successful transformation with *Agrobacterium*. *Camelina sativa* seeds have a 0.5-1 mm thick hygroscopic polysaccharide surface around the seed protecting the seed for example against fungal and bacterial spores and requiring more effective surface sterilization compared to many other species. Seeds were first optionally sterilized and subsequently germinated and grown on Murashige and Skoog (MS) agar medium or an equivalent plant growth medium. Preferably the leaf segments of 2-3 weeks, but preferably 10-20 days old *Camelina sativa* plants preferably grown in vitro were used in the *Agrobacterium*-mediated transformation. Leaf segments were excised and then placed on cultivation medium, preferably Murashige and Skoog (MS) agar medium or an equivalent medium, supplemented with hormones, such as cytokinins and/or auxins or other hormones and sucrose or other sugar source and cultivated on said medium for 24 hours.

The *Camelina sativa* explants were inoculated by immersing explants in liquid Murashige and Skoog (MS) medium or an equivalent medium or water containing *Agrobacterium* carrying the selected transformation vector with at least one gene foreign to said *Camelina sativa*.

After removing the redundant liquid on the immersed segments the explants were placed on solid Murashige and Skoog (MS) medium or an equivalent supplemented with hormones, such as cytokinins or auxins, and optionally with acetosyringone for co-cultivation. Explants were co-cultivated with *Agrobacterium* for 2 days (48 hours) or a time sufficient to enable the transformation. During this step, the *Agrobacterium* transferred the foreign gene construct into *Camelina sativa* cells. The co-cultivated segments were then washed and placed on Murashige and Skoog (MS) medium agar or equivalent medium for callus and shoot regeneration. Optional antibiotic selection begins preferably immediately after transformation and the result of the selection can be seen in 1-2 weeks, when explants begin to form callus. Selection was carried out using optional antibiotics such as kanamycin, hygromycin or other selective agents for optionally 4-20 days or longer. An efficient transformation was also obtained without selection with antibiotics.

When the selection had been completed the leaf segments had also produced callus and shoots and roots. The regenerated, transgenic shoots were grown and rooted for about 2-3 weeks on Murashige and Skoog (MS) medium or equivalent medium, which is hormone-free or optionally supplemented with auxins, including, but not limited to, indole-3-acetic acid (IAA), 4-chloro-IAA, phenylacetic acid, α-naphthaleneacetic acid (NAA) and/or 2,4-dichlorophenoxyacetic acid (2,4-D).

After rooting shoots were transferred to soil and transgenic plants were grown in greenhouse conditions (FIG. 5). Plants were tested for GUS expression with a histological GUS assay and the presence of the transgene was confirmed with PCR and Southern blot analysis.

The invention comprises a mechanism for carrying out *Agrobacterium*-mediated genetic transformation test kit, being packaged combination including one or more optionally sterilized seeds to provide seedlings from which explants of *Camelina sativa* are obtainable, an *Agrobacterium* vector, at least one DNA sequence encoding a desired gene product as such or in a recombinant DNA construct comprising *Agrobacterium* and/or plasmids and at least one DNA sequence encoding the desired gene product functionally combined with sequences responsible for or capable of regulating said functions, and optionally at least one sequence allowing selection of explants of *Camelina sativa* with a culture of *Agrobacterium* carrying the said recombinant DNA construct, one or more cell culture mediums supplemented or non-supplemented optionally with at least one hormone and/or growth factor and/or at least one selective component which is capable of selecting plant cells transformed with the said construct. The system also comprises the means and the method for obtaining whole transgenic *Camelina sativa* plants and growing them in vitro and in greenhouse including appropriate growth media, soil and equivalents.

The invention is described in more detail in the following experimental part. The scope of the invention is naturally not restricted to these methods, one skilled in the art can easily replace the suggested materials and methods with alternatives.

Materials and Methods

Plant material. The seeds of *Camelina sativa* were sterilized for 1 min in 70% ethanol and 10 min in Na-hypochlorite (3% active Cl⁻) with addition of Tween-20, and washed three times in sterile water. The sterilized seeds were grown on Murashige and Skoog (MS; Murashige and Skoog, Physiol Plant. 15:472-493, 1962) agar medium or an equivalent medium without sugars. The leaves of 2-3 weeks old, preferably 10-20 days old, in vitro plants were used in the transformation experiments.

*Agrobacterium* vectors. *Agrobacterium tumefaciens* strain C58C1 containing the plasmid pGV3850 (Zambryski et al., EMBO J. 2:2143-2150, 1983), strain EHA105 (Hood et al., Transgenic Res. 2:208-218, 1993) with the plasmid pTiBo542 and strain LBA4404 with pAL4404 (Hoekema et al., Nature 303:179-180, 1983) were tested for transformation of *Camelina sativa*. The uidA marker gene (β-glucuronidase, GUS) containing an intron (uidA-int) (Vancanneyt et al., Mol. Gen. Genet. 220:245-250, 1990) was cloned into all vectors containing T-DNA region as listed above. The uidA-intron-containing gene was used to prevent bacterial GUS expression and enabled the testing of GUS-activity at an early stage of transformation. The co-integrative pHTT294 vector, essentially similar to pHTT370 (Elomaa et al., Bio/Technology 11:508-511, 1993) carrying the uidA-intron-containing gene under the CaMV 35S promoter (Datla et al., Plant Sci. 94:139-149, 1993), was transferred to an *Agrobacterium* strain C58C1. Binary pGPTV-HPT and pGPTV-KAN vectors (Becker et al., Plant. Mol. Biol. 20:1195-1197, 1992) with the uidA gene exchanged for the uidA-intron-containing gene under the control of the 35S promoter of CaMV were transformed into *Agrobacterium tumefaciens* strains EHA105 and LBA4404.

*Agrobacterium tumefaciens* was grown overnight in liquid YEB (Lichtenstein and Draper, Genetic Engineering of Plants. In: Glover DM (ed.) DNA cloning—a practical approach, vol. 2. Oxford IRL, Oxford, pp 67-119, 1985) medium with shaking supplemented with appropriate antibiotics for each strain. An aliquot (1/100 vol/vol) of the overnight culture was then inoculated in fresh YEB medium with appropriate antibiotics and bacteria were grown overnight with shaking. An *Agrobacterium tumefaciens* culture of $OD_{600}=1.0$ was used for transformation.

Culture Medium

Composition of Murashige and Skoog (MS) plant growth medium:

| Salts: | g/l | Vitamins: | mg/l |
|---|---|---|---|
| $NH_4NO_3$ | 1.65 | Thiamine | 0.1 |
| $KNO_3$ | 1.9 | Pyridoxine | 0.1 |
| $MgSO_4 \times 7H_2O$ | 0.37 | Nicotinic acid | 0.5 |
| $KH_2PO_4$ | 0.17 | Myo-inositol | 100 |
| $CaCl_2 \times 2H_2O$ | 0.44 | Glycine | 2.0 |
| | mg/l | | mg/l |

-continued

| | | | |
|---|---|---|---|
| $H_3BO_3$ | 6.2 | Sucrose | 2.0 |
| $MnSO_4 \times 4H_2O$ | 22.3 | Agar | 7.0 |
| Kuvshinov 4 divisional | | | |
| $ZnSO_4 \times 7H_2O$ | 8.6 | | |
| KJ | 0.83 | pH 5.6 | |
| $Na_2MoO_4 \times 2H_2O$ | 0.25 | | |
| $CuSO_4 \times 5H_2O$ | 0.025 | | |
| $CoCl_2 \times 2H_2O$ | 0.025 | | |

Plant transformation. Leaf segments of in vitro grown *Camelina sativa* plants (FIG. 1) were cultivated for 24 hours on Murashige and Skoog (MS) medium or an equivalent medium supplemented with 0.7% agar. All MS culture media were supplemented with 2% sucrose and all in vitro cultures were kept at temperatures of 25° C. (day) and 18° C. (night) under 16 h photoperiod. Subsequently, the explants were immersed for 1-3 min in Murashige and Skoog (MS) solution or an equivalent which had been inoculated with a dilution (e.g. 1/10 vol/vol) of an overnight culture of *Agrobacterium tumefaciens*. Thereafter, redundant liquid present on the surface of leaf segments was removed using filter paper and the explants were placed on the Murashige and Skoog (MS) agar medium supplemented with auxin and cytokinin hormones, 6-benzylaminopurine (BAP) and alpha-naphthaleneacetic acid (NAA), for co-cultivation with bacteria for 2 days. After co-cultivation, the explants were washed with water containing cefotaxime (Claforan) (700 mg/l), carbenicillin (200 mg/l) or ticarcillin/clavulanic acid (Duchefa) (100 mg/l). The surfaces of the explants were dried on filter paper and placed on the Murashige and Skoog (MS) medium or an equivalent medium for selection and shoot regeneration. The medium was supplemented with the same hormones and antibiotics than for transgenic tissue selection (kanamycin, hygromycin) and *Agrobacterium* growth inhibitors.

Selection and regeneration. Eventually, cultivation of the explants for two weeks on Murashige and Skoog (MS) medium or an equivalent medium supplemented with 0.5-1.5 mg/l 6-benzylaminopurine (BAP) and 0.1-0.5 mg/l alpha-naphthaleneacetic acid (NAA) was found to be best for callus, shoot and root formation. Thereafter, the whole explants or cut shoots were transferred to Petri dishes containing hormone-free culture medium, preferably Murashige and Skoog (MS) medium or an equivalent medium, where recovered shoots elongated and started to root. In the case that the explant forms both shoots and roots simultaneously, whole explant is preferably transferred onto Murashige and Skoog (MS) agar medium or an equivalent medium supplemented with cytokinins [1 mg/ml 6-benzylaminopurine (BAP)] to stimulate further growth of shoots. Petri dishes were sealed with porous paper tape. Recovered transgenic shoots were grown on Murashige and Skoog (MS) medium or an equivalent medium without hormones or optionally supplemented with 0.1-0.2 mg/l α-naphthaleneacetic acid (NAA) for stimulation of rooting, stem elongation and micropropagation. The exact hormone concentrations varied for different cultivars tested. Selection using hygromycin or alternatively kanamycin was applied preferably immediately after co-cultivation of the explants with *Agrobacterium tumefaciens*. Antibiotics were used in concentrations ranging between 15-25 mg/l. Selection with an antibiotic was carried out for 4-10 days after co-cultivation. It could be seen already after 5-7 days that the leaf segments produced callus and transgenic shoots.

Analysis of transgene expression. The histological GUS assay was performed on transformed callus and leaf tissue. The uidA-intron-containing gene was used to prevent bacterial GUS expression in transformation and to enable testing of GUS activity at early stages of transformation, even immediately after co-cultivation with *Agrobacterium tumefaciens*. Usually in the optimization experiments, GUS assay was performed 4-7 days after co-cultivation with *Agrobacterium tumefaciens*.

The transgenic plants which showed stable GUS expression and grew well after selection were grown in the greenhouse (FIG. 5) They were then used for PCR and Southern blot analysis to confirm the transformation event at the DNA level.

Southern blot analysis was performed using a coding sequence of uidA gene labeled with digoxigenin-11-UTP to obtain an RNA probe according to the manufacturer's instructions (Boehringer Mannheim). Three μg of DNA from *Camelina sativa* plants which showed stable GUS expression was digested with EcoRI and BamHI restriction enzymes. These enzymes cut out a 2 kb uidA gene fragment from the T-region of pGPTV-HPT or pGPTV-KAN inserted in the Camelina sativa genome.

Results of the Preliminary Experiments in Developing the Transformation Method

Source plants. Field-grown *Camelina sativa* plants produce seed heavily contaminated and were practically improper for use in the transformation, because leaf explants contained bacteria which prevented successful transformation by *Agrobacterium tumefaciens*. To achieve good starting material seed producing *Camelina sativa* plants were grown in greenhouse conditions. The seeds, which had been developed and matured in greenhouse, were free of contaminations after surface sterilization. *Camelina sativa* seeds have a hygroscopic polysaccharide surface, which forms a 0.5-1 mm barrier around the seed. This barrier protects the seed against fungal and bacterial spores. This particular characteristics of *Camelina sativa* seed surface requires more effective surface sterilization of seeds compared to many other species. The sterilization experiments were performed as shown in Table 1. The *Camelina sativa* seeds were immersed in 70% ethanol for 1 min and treated with Na-hypochlorite solution with an addition of Tween-20 (1 drop per 100 ml).

TABLE 1

Seed germination (%) and contamination after different surface sterilization treatments. Concentration of Na-hypochlorite is shown in columns as % of active Cl. The time of treatment with Na-hypochlorite is shown in rows.

| | % Na-hyp. | | |
|---|---|---|---|
| Time min. | 1% Cl⁻ | 3% Cl⁻ | 6% Cl⁻ |
| 5 min. | Contaminat. | 100% | 60% |
| 10 min. | 100% | 100% | 30% |
| 20 min. | 100% | 60% | 0% |

After sterilization the seeds were washed three times in sterilized water and placed on Murashige and Skoog (MS) agar medium or an equivalent medium without sugars for germination. Germination was assessed 3 days after sterilization. The 10 min treatment with 3% Na-hypochlorite was found optimal for *Camelina sativa* seed sterilization.

Sterilized seeds were germinated and grown for 2-3 weeks or preferably 10-20 days on Murashige and Skoog (MS) agar medium or an equivalent medium without sucrose and hormones. The green leaves served as a source for explants for the transformation.

Plant transformation. Three different *Agrobacterium tumefaciens* strains, namely C58C1, EHA105 and LBA4404 were tested. C58C1pGV3850 harbors the cointegrative vector pHTT294. The strains EHA105 and LBA4404 carried the binary vector pGPTV-HPT. UidA-intron-containing reporter gene was cloned from pGUS-int into all the binary and cointegrative vectors used in the transformation experiments. The uidA-int gene was placed under CaMV 35S promoter.

Hypocotyl, cotyledon, leaf and stem segments were tested for affinity to *Agrobacterium tumefaciens*. The cotyledon and leaf segments had the best transformation capacity. Because of their better regeneration ability, leaf segments were used in further transformation experiments. Leaves of in vitro grown *Camelina sativa* plants are rather small in size: 2 to 4 cm long and 0.5-1 cm wide. Therefore, narrow leaves were cut only across the leaf while larger leaves were also cut in half along the central vein.

Figure 3A:
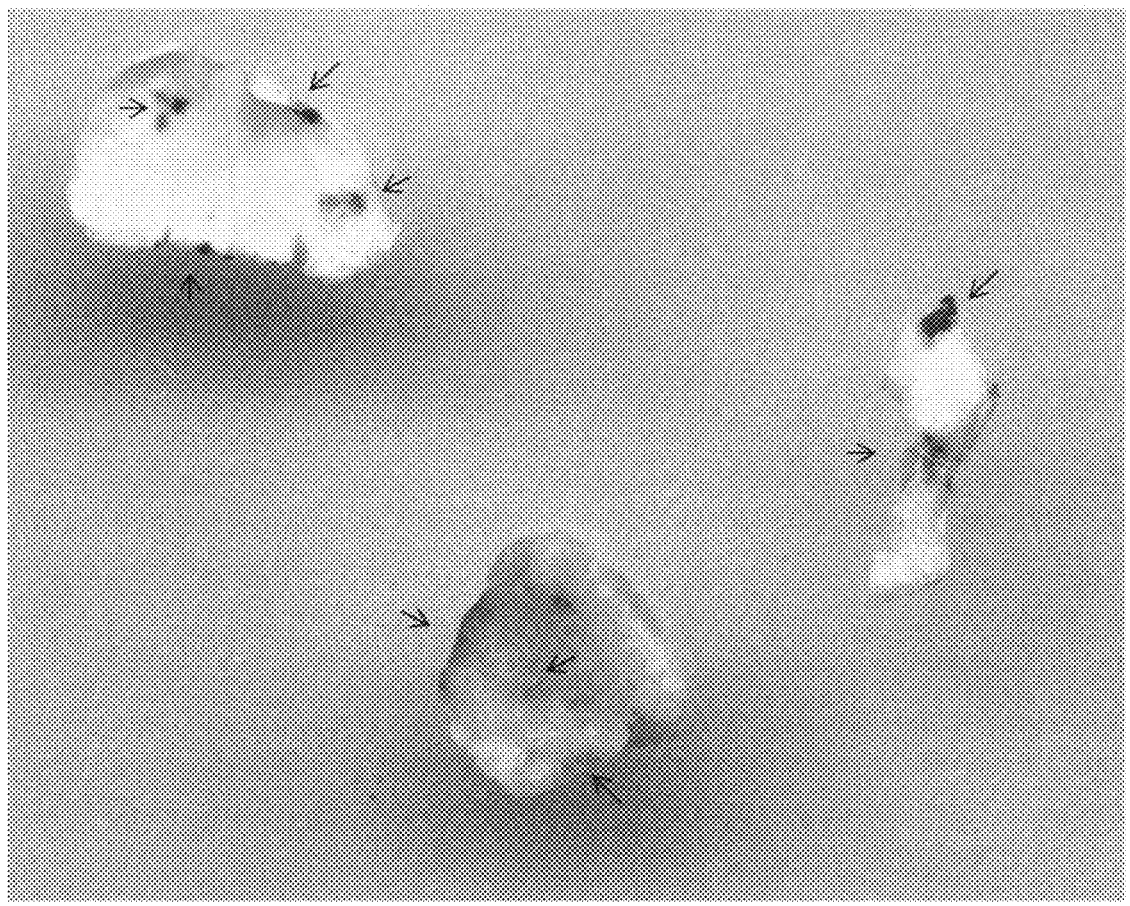
FIG. 3a depicts GUS expression in callus tissue of *Camelina sativa*. The arrowheads point to GUS stained inclusions.
Figure 3B:
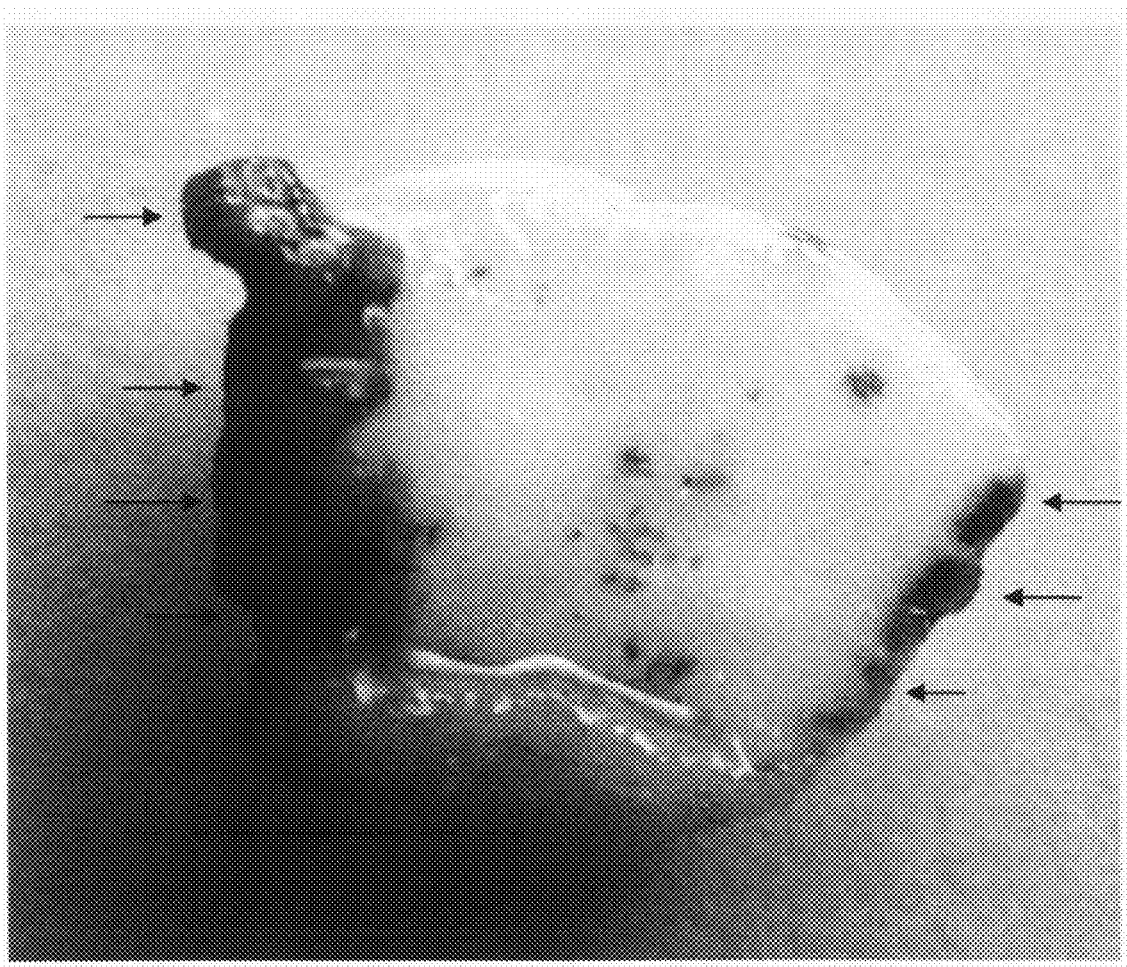
FIG. 3b depicts GUS expression in callus tissue of *Camelina sativa*. The arrowheads point to GUS stained inclusions.

Transformation efficiencies of different *Agrobacterium tumefaciens* strains were measured as a proportion of blue inclusions in callus one week after inoculation of leaf segments (FIG. 3a, 3b).

TABLE 2

Transformation efficiencies of different *Agrobacterium tumefaciens* strains. First column: GUS positives/all explants, Second column: number of intensively transformed explants/all explants. The third column gives the transformation percentage and the percentage of intensive transformation.

| Agrobacterium | Blue inclusions all explants | Intensively transformed | Transformation % (intensive) |
|---|---|---|---|
| LBA4404pGPTV-HPT | 35/50 | 7/50 | 70% (14) |
| EHA105pGPTV-HPT | 24/50 | | 48% (0) |
| C58C1pGV3850 pHTT294 | 33/50 | 4/50 | 66% (8) |

The results of the three transformation experiments, summarized in Table 2, showed that LBA4404 and C58C1pGV3850 strains were effective in transforming *Camelina sativa*. EHA105 was slightly less effective. The explants infected with LBA4404 or C58C1 strains had large intensively stained blue inclusions. Thus, the strains LBA4404 and C58C1 were used in subsequent transformation experiments.

Figure 2:
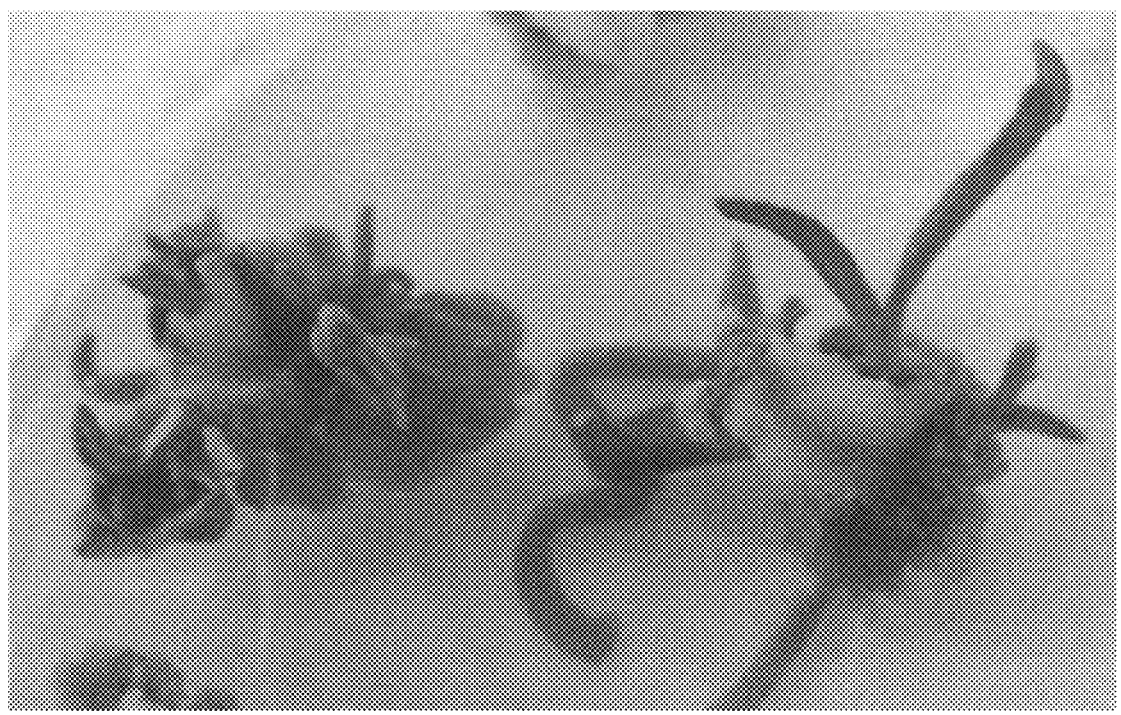
FIG. 2 shows regenerated shoots of *Camelina sativa* on leaf segment explants.

Shoot regeneration. Effects of different hormones on various explants of *Camelina sativa* (hypocotyl, cotyledon, leaf and stem segments) were tested in preliminary experiments to achieve sufficient shoot regeneration. 6-benzylaminopurine (BAP) and α-naphthaleneacetic acid (NAA) were more effective to induce shoot and root regeneration than kinetin and indole-3-acetic acid (IAA). The regeneration capacity of cotyledons was 30-50% whereas shoots from hypocotyl and stem segments did not regenerate. The best regeneration (100%) was achieved with leaf segments (FIG. 2). The 2,4-dichlorophenoxyacetic acid (2,4-D), gibberellins as well as silver nitrate treatments did not have an effect on shoot regeneration. The best regeneration was achieved with a certain ratio of auxin and cytokinin hormones. For example, the best shoot regeneration of leaf segments of *Camelina sativa* variety cv. Calena was achieved with the hormone combination of 1 mg/l 6-benzylaminopurine (BAP) and 0.2 mg/l α-naphthaleneacetic acid (NAA), while the optimal combination for *Camelina sativa* variety cv. Calinca was 0.7 mg/l 6-benzylaminopurine (BAP) and 0.3 mg/l α-naphthaleneacetic acid (NAA).

Recovered shoots had a tendency for inflorescence formation and had problems with rooting. To overcome these problems, recovered shoots were cultivated subsequently on Murashige and Skoog (MS) medium or an equivalent medium optionally supplemented with auxins (e.g. indole-3-acetic acid (IAA) 1 mg/l). Another way was to regenerate shoots and roots simultaneously with the hormone combination of 0.5-1 mg/l 6-benzylaminopurine (BAP) and 0.2-0.7 mg/l α-naphthaleneacetic acid (NAA).

Several different factors were tested for impact on shoot regeneration efficiency. Optimal parameters were found for pH (5.6-5.8), for sucrose content (2-3%), and solidifiers (0.7% agar). Modifications in the concentration of $NH$, $NO-$, $K^+$ and $Ca^{2+}$ ions in the standard Murashige and Skoog (MS) medium had no effect nor did the Addition of glucose. Culturing the explants on the B5 medium had also no effect on shoot regeneration.

Selection. To prevent *Agrobacterium tumefaciens* growth on the medium, cefotaxime (Claforan) (500 mg/l), carbenicillin (200 mg/l), ticarcillin/clavulonic acid (Duchefa) (100 mg/ml) or vancomycin (200 mg/ml) were used.

The selection markers i.e. the hpt and nptII genes in transformation constructs provided the plants with resistance to hygromycin and kanamycin, respectively. It had been found that the application of a selection pressure (15-20 mg/l, preferably 10-20 mg/l of antibiotic) preferably for 4-10 days after washing of the *Agrobacterium tumefaciens* from explants is optimal. First regenerative primordia form on the calli already 10 days after cutting of the leaf segments, and selection of transformed tissues should be performed before that. It was found in preliminary experiments that 5-15 mg/l antibiotic prevented morphogenesis of explants. Selection of transformed tissue using 5-10 mg/l hygromycin or kanamycin was not enough. On the other hand, the concentrations of the antibiotic higher than 20-30 mg/l killed the explants too fast for any shoots to recover.

Analysis of Transformation

The histological GUS assay was performed on transformed callus and leaf tissue. To prevent GUS expression in *Agrobacterium tumefaciens*, the uidA gene containing the intron was used in transformation experiments. It enabled the testing of GUS activity almost immediately after co-cultivation with *Agrobacterium tumefaciens*. Usually, GUS assay was made 4-7 days after co-cultivation with *Agrobacterium tumefaciens* during the optimization of transformation (FIG. 3). The assay was also performed on regenerated primordia and shoots as well as leaf segments of recovered plants.

Example 1

Figure 1:
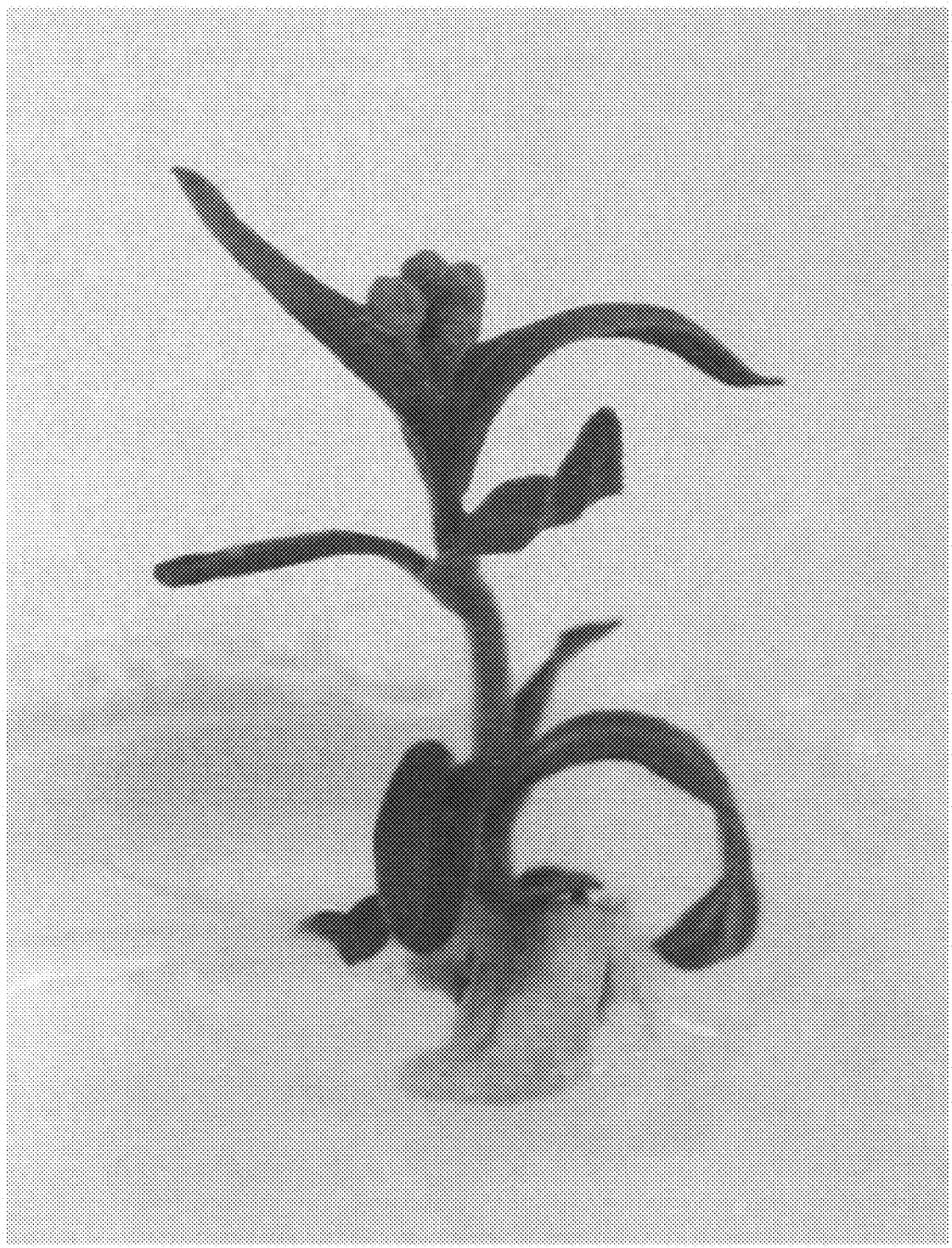
FIG. 1 shows in vitro cultured *Camelina sativa* plant.

Transformation Protocol for *Camelina sativa* cv. Calena with *Agrobacterium tumefaciens* Strain LBA4404 Harboring the Binary Plasmid pGPTV-HPT with uidA Intron Containing Gene The seeds of *Camelina sativa* plant grown in greenhouse were sterilized by immersing in 70% ethanol for 1 min and then treating for 10 min with Na-hypochlorite solution (3% active $Cl^-$) with an addition of Tween-20 (1 drop per 100 ml). After sterilization the seeds were washed three times in sterile water and placed on solid Murashige and Skoog (MS) agar medium (Murashige and Skoog, Physiol. Plant. 15:472-493, 1962) without sugars for germination. Sterilized seeds were germinated and grown 2-3 weeks on solid Murashige and Skoog (MS) medium without hormones (FIG. 1). Green leaves served as a source of explants for transformation procedure.

*Agrobacterium tumefaciens* strain LBA4404 carrying pGPTV-HPT-GUSint vector was grown overnight at 28° C. with shaking in liquid YEB medium (Lichtenstein and Draper, Gene Engineering of Plants. In: Glover DM (ed.) DNA Cloning—A Practical Approach, vol. 2. Oxford IRL, Oxford, pp 67-119, 1985) supplemented with 50 mg/l kanamycin and rifampicin. Subsequently an aliquot of the culture (1/100 v/v) was inoculated in fresh YEB medium supplemented with 50 mg/l kanamycin and rifampicin and the bacteria were grown overnight with shaking. *Agrobacterium* culture of $OD_{600}=1.0$ was used in the transformation experiments.

Narrow leaves of in vitro grown *Camelina sativa* plants were cut only across the leaf blade, whereas large leaves were additionally cut in half along the central vein. The leaf segments were cultivated for 24 hours on Murashige and Skoog (MS) 0.7% agar medium supplemented with 1 mg/l 6-benzylaminopurine (BAP) and 0.2 mg/l α-naphthaleneacetic acid (NAA). All the Murashige and Skoog (MS) culture media were supplemented with 2% sucrose and all in vitro cultures were kept at temperatures of 25° C. (day) and 18° C. (night) under the photoperiod of 16 h. The explants were immersed for 1-3 min in Murashige and Skoog (MS) solution inoculated with a dilution (e.g. 1/10 v/v) of the overnight culture of *Agrobacterium tumefaciens* LBA4404. Redundant liquid on the stem segments was removed using filter paper and the explants were placed on Murashige and Skoog (MS) agar medium supplemented with auxin and cytokinin for co-cultivation with bacteria for 2 days. The explants were washed with water containing claforan [cefotaxime] (700 mg/l)] or carbenicillin (700 mg/ml). The surfaces of the explants were dried on filter paper and the explants were placed on Murashige and Skoog (MS) medium supplemented with hormones [0.7 mg/l 6-benzylaminopurine (BAP), 0.25 mg/l α-naphthaleneacetic acid (NAA)] and 200 mg/l carbenicillin or claforan and 15 mg/ml hygromycin. Two to three weeks old shoots (FIG. 2) were placed to the normal or half strength Murasghige and Skoog (MS) medium solidified with 0.7% agar and supplemented with 200 mg/l carbenicillin or cefotaxime and optionally with 15 mg/l hygromycin and auxin [indole-3-acetic acid (IAA) 0.5-1 mg/l] shoots were transferred to soil and transgenic plants were grown in greenhouse conditions (FIG. 5). Transgenic plants were tested for uidA (GUS) gene expression with a histological GUS assay and the presence of the transgene was confirmed with Southern analysis.

Example 2

Transformation Protocol for *Camelina sativa* cv. Calinca with *Agrobacterium tumefaciens* Strain C58C1 pGV3850 Harboring the Binary Ti Vector with Kanamycin Selection Seeds were taken from greenhouse grown *Camelina sativa* cv. Calinca plants (no older than 4 months). Transformation efficiency increases from 66% to 100% if donor plants are grown in greenhouse.
10 Days Before Excision of the Explants.
Seeds of *Camelina sativa* were sterilized and placed in vitro on Murashige and Skoog (MS) agar medium without sucrose and grown at temperatures of 25° C. (day) and 18° C. (night) as described in Example 1.
$1^{st}$ Day.
A fresh colony of *Agrobacterium tumefaciens* strain C58C1pGV3850 carrying binary pGPTV-KAN vector (Becker et al., Plant Mol. Biol. 20:1195-1197, 1992) containing uidA-int gene under 35S promoter and selectable marker gene nptII, was inoculated in 3 ml of liquid YEB medium supplemented with 25 mg/l rifampicin (Rif) and 50 mg/l kanamycin (Kan). The bacteria were grown overnight with shaking at 28° C.
$2^{nd}$ Day. Pre-Cultivation.

The first leaves (no cotyledons) of in vitro grown *Camelina sativa* were cut into segments across the leaf and were placed on pre-cultivation plates containing 0.7% MS agar medium supplemented with 2% sucrose, 0.7 mg/l 6-benzylaminopurine (BAP) and 0.3 mg/l alpha-naphthaleneacetic acid (NAA). All dishes were sealed with porous paper tape (Micropore 3M). A 30 μl aliquot of overnight culture of the *Agrobacterium tumefaciens* was inoculated in 3 ml of fresh YEB medium supplemented with rifampicin (Rif) and kanamycin (Kan).
3rd Day. *Agrobacterium tumefaciens* Inoculation.

The explants were immersed in liquid Murashige and Skoog (MS) medium supplemented with 2% sucrose and inoculated with a 1/10 (v/v) dilution of the overnight culture of *Agrobacterium tumefaciens*. After 5 min inoculation redundant liquid on the explants was removed using sterilized filter paper.

The explants were placed on Murashige and Skoog (MS) medium supplemented with 2% sucrose for co-cultivation with the *Agrobacterium tumefaciens* for two days at 28° C. in dim light.
$5^{th}$ Day. Washing and Selection.

The explants were washed with water containing 100 mg/l ticarcillin/clavulanic acid (Duchefa). Ticarcillin (Tc) has less negative effect on shoot and root regeneration than cefotaxime (Claforan) and carbenicillin. On the other hand it is more effective growth inhibitor of *Agrobacterium tumefaciens* than vancomycin. The explants were dried on the filter paper and transferred onto selection medium containing 0.7% Murashige and Skoog (MS) agar medium supplemented with 2% sucrose, 0.7 mg/l 6-benzylaminopurine (BAP), 0.3 mg/l α-naphthaleneacetic acid (NAA), 15 mg/l kanamycin and 50 mg/l ticarcillin/clavulanic acid (Duchefa). The explants were cultured on the selection medium for 4-5 days.
$10^{th}$ Day. Regeneration.

The explants were transferred onto plates containing 0.7% MS agar medium supplemented with 2% sucrose, 0.7 mg/l 6-benzylaminopurine (BAP), 0.3 mg/l α-naphthaleneacetic acid (NAA), and 50 mg/l ticarcillin/clavulanic acid (Duchefa) for shoot and root regeneration for 10-14 days. Tall (3 cm high) plates were sealed with porous paper tape to increase aeration. Simultaneous regeneration of shoots and roots is preferable for effective recovery of transgenic *Camelina sativa* plants.
20-$24^{th}$ Day. Shoot and Root Elongation.

Explants forming 0.5-1 cm long leaves (shoots) and roots were transferred on 0.7% Murashige and Skoog (MS) agar medium containing 2-3% sucrose and 100 mg/l ticarcillin/clavulanic acid without hormones or optionally supplemented with 1 mg/ml 6-benzylaminopurine (BAP) for 5-7 days. Alternatively explants were transferred to fog system (mist chamber) in greenhouse for consecutive growth.
25-$30^{th}$ Day. Transgenic Plant Growth.

Successfully grown and rooted shoots were transferred to soil without separation from explants. Shoots in pots were placed into closed chamber. The chamber was opened gradually day by day to increase aeration. Alternatively explants were transferred to fog system (mist chamber) in greenhouse for consecutive growth. The recovered shoots formed inflorescence and seedpods. Plant tissues were tested for expression of marker gene (GUS) with GUS assay, PCR and Southern blot.

Example 3

Transformation Protocol for *Camelina sativa* cv. Calena with *Agrobacterium tumefaciens* Strain C58C1 pGV3850 Harboring Cointegrative Ti DNA without Selection of Transgenic Tissues Seeds were taken from greenhouse grown *Camelina sativa* cv. Calena plants (no older than 4 months). Transformation efficiency increases from 66% to 100% if donor plants are grown in greenhouse.

10 Days Before Explants Excision.

Seeds were sterilized and placed in vitro on Murashige and Skoog (MS) medium without sucrose and grown at temperatures of 25° C. (day) and 18° C. (night) as described in Example 1.

1$^{st}$ Day.

A fresh colony of C58C1pGV3850 with interned Ti DNA from pHTT-HPT (Elomaa et al., Bio/Technology 11:508-511, 1993) vector containing GUS gene under 35S promoter and hpt selectable marker was inoculated in 3 ml of liquid YEB supplemented with 25 mg/l rifampicin (Rif) and 100 mg/l spectinomycin (Spe) or streptomycin (Str). The bacteria were grown overnight with shaking at 28° C.

2$^{nd}$ Day. Pre-Cultivation.

The first leaves (no cotyledons) were cut into segments across the leaf and placed onto the pre-cultivation plates containing 0.7% Murashige and Skoog (MS) agar medium with 2% sucrose supplemented with 1 mg/l 6-benzylaminopurine (BAP) and 0.5 mg/l Â-naphthaleneacetic acid (NAA). All plates were sealed with porous paper tape (Micropore 3M).

A 30 µl aliquot of overnight culture of the *Agrobacterium tumefaciens* was inoculated in 3 ml of fresh YEB medium supplemented with rifampicin (Rif), spectinomycin (Spe) or streptomycin (Str).

3$^{rd}$ day. *Agrobacterium* Inoculation.

The plant explants were immersed in liquid Murashige and Skoog (MS) medium supplemented with 2% sucrose and inoculated with a 1/10 dilution of the overnight culture of *Agrobacterium tumefaciens*. Redundant liquid on the explants was removed on sterilized filter paper. The explants were co-cultivated with the *Agrobacterium tumefaciens* for two days at 28° C. in dim light.

5$^{th}$ Day. Washing and Regeneration.

The explants were washed with water containing 100 mg/l ticarcillin/clavulanic acid (Duchefa). Ticarcillin (Tc) has less negative effect on shoot and root regeneration compared to cefotaxime (Claforan) and carbenicillin. On the other hand it is more effective growth inhibitor of *Agrobacterium tumefaciens* than vancomycin. The explants were dried on the filter paper. Then the explants were placed onto selection medium plates containing 7% Murashige and Skoog (MS) agar medium with 2% sucrose supplemented with 1 mg/l 6-benzylaminopurine (BAP), 0.5 mg/l α-naphthaleneacetic acid (NAA) and 50 mg/l ticarcillin/clavulanic acid (Duchefa) 0.5 mg/l for shoot and root regeneration for 2-3 weeks. Tall (3 cm high) plates were sealed with porous paper tape to increase aeration.

20-24$^{th}$ Day. Shoot and Root Elongation.

Explants forming 0.5-1 cm long leaves (shoots) and roots were transferred onto 0.7% Murashige and Skoog (MS) agar medium containing 2% sucrose supplemented with 100 mg/l ticarcillin/clavulanic acid (Duchefa) without hormones or with 1 mg/ml 6-benzylaminopurine (BAP) for 5-7 days. Plates were not sealed with tape.

Regenerated shoots were tested for GUS expression with histological GUS assay. GUS activity was seen in 4 shoots out of 123. It means that average of about 3% of shoots regenerated after transformation were transgenic without the use of antibiotic selection. Thus the method can be used for producing transgenic *Camelina sativa* plants free from antibiotic resistance genes or selectable marker genes.

The strain C58C1pGV3850 was the most effective for transformation of *Camelina sativa*. 100% of the explants were transformed. The average proportion of tissue in each explant showing GUS expression was more than 30%. This is the highest level of transformation that was registered by present inventors. The transformation efficiency enables to obtain transgenic plats without antibiotic or other selection of transgenic plants.

Example 4

Analysis of Transformation

The histological GUS assay was performed on transformed callus and leaf tissue. To prevent GUS expression in Agrobacteria the uidA gene containing an intron was used in transformation experiments. It enabled the testing of GUS activity even immediately after co-cultivation with *Agrobacterium tumefaciens*. Usually, GUS assay was made 4-7 days after co-cultivation with *Agrobacterium tumefaciens* during the optimization of transformation (FIG. 3). The assay was also performed on regenerated primordia and shoots as well as leaf segments of recovered plants.

Transgenic plants which showed steady positive GUS expression and grew well under selection conditions were used for PCR analysis of transgene insertion and Southern blot analysis to confirm the transformation events.

PCR Analysis

Total genomic DNA was isolated from leaf tissue of transgenic and non-transgenic *Camelina sativa* plants using DNeasy Plant Mini Kit according to the supplier's instructions (Qiagen). The presence of the uidA and hpt gene in the GUS positive plants was determined by PCR analysis using 24 nucleotides long primers specific to the coding sequences of uidA and hpt genes. PCR reaction mix contained approximately 1 ng/µl of template DNA and DyNAzyme polymerase (Finnzymes) was used for amplification. PCR program consisted of: 94° for 2 min; 30 cycles of 94° C. for 30 sec, 48° C. for 30 sec and 72° C. for 2 min. Three µl of PCR reaction mixture was run in 0.8% agarose gel containing ethidium bromide at 100 V. No PCR product was obtained when non-transgenic Camelina sativa DNA was used as template, whereas when using transgenic *Camelina sativa* an amplification product of 700 nucleotides corresponding to the positive control was obtained which confirmed the presence of transgene in transgenic *Camelina sativa* plants (FIG. 4).

Southern Analysis

Total genomic DNA was isolated from leaf tissue of *Camelina sativa* plants using DNeasy Plant Midi Kit according to the supplier's instructions (Qiagen). Three µg of DNA from GUS positive *Camelina sativa* plants was digested with EcoRI and BamHl restriction enzymes. These enzymes cut out a 2 kb uidA gene fragment from the T-region of pGPTV-KAN (-HPT) inserted in the plant genome. Digested DNA samples were separated in a 0.7% agarose (Promega) gel overnight at 15 mA current and transferred to positively charged nylon membrane (Boehringer Mannheim) using vacuum blotter. RNA probes were synthesized using T3 RNA polymerase on the pBluescript vector carrying uidA or hpt gene sequence and labeled with digoxigenin-11-UTP. The membrane was hybridized and developed according to the supplier's instructions (Boehringer Mannheim, The DIG user's guide for filter hybridization). The membrane was prehybridized at 50° C. for 2 h and hybridized at 50° C. in a "DIG Easy Hyb" hybridization solution (Boehringer Mannheim) overnight with a digoxigenin-UTP labeled RNA probe. The concentration of RNA probe was 100 ng/ml. After hybridization the membrane was washed in SSC buffers, blocked and detected using "Anti-Digoxigenin-AP alkaline phosphatase (Boehringer Mannheim). Chemiluminescent detection was done with CSPD-substrate and the membrane was exposed to X-ray film (Boehringer Mannheim). Presence of the transgene insertion was proved in comparison to DNA of non-transgenic *Camelina sativa* plant DNA as negative control, and to plasmid DNA carrying the gene sequence mixed with non-transgenic plant DNA as positive control.

What is claimed is:

1. A method for genetically transforming a *Camelina sativa* plant comprising the steps of:
   a) collecting *Camelina sativa* seeds from a plant grown in green house or growth chamber,
   b) sterilizing the seeds and growing seedlings in vitro;
   c) providing explants from in vitro grown *Camelina sativa* leaves;
   d) inoculating the explants with *Agrobacterium* strain containing at least one recombinant DNA construct and optionally a selection marker;
   e) allowing transformation to take place on culture medium supplemented with 2% sucrose;
   f) inducing formation of one or more shoots and roots from transformed explants on a cell culture medium, said medium containing 2% sucrose;
   g) allowing elongation of transgenic shoots and roots on a medium containing 2-3% sucrose; and
   h) growing the shoots into transgenic *Camelina sativa* plants.

2. The method of claim 1, wherein *Agrobacterium* strain of step d is free from selection markers.

3. The method of claim 1, wherein the recombinant DNA construct contains a sequence encoding a homologous or heterologous gene product.

4. The method of claim 2, wherein the recombinant DNA construct contains a sequence encoding a homologous or heterologous gene product.

5. The method of claim 1, wherein the transgenic *Camelina sativa* cell or cell line is produced.

6. The method of claim 2, wherein the transgenic *Camelina sativa* cell or cell line is produced.

7. The method of claim 1, wherein the transgenic *Camelina sativa* seed is produced.

8. The method of claim 7, wherein the seed contains heterologous or homolgous recombinant products.

9. The method of claim 2, wherein the transgenic *Camelina sativa* seed is produced.

10. The method of claim 9, wherein the seed contains heterologous or homologous recombinant products.

* * * * *